United States Patent
Long et al.

(10) Patent No.: US 7,307,257 B2
(45) Date of Patent: Dec. 11, 2007

(54) METHOD AND APPARATUS FOR ON-LINE MEASUREMENT OF POLYMER PROPERTIES

(75) Inventors: Robert L. Long, Houston, TX (US); Stephen K. Morgan, Deham Springs, LA (US); Carl J. Thomas, Baton Rouge, LA (US); Oscar K. Broussard, III, Baton Rouge, LA (US)

(73) Assignee: ExxonMobil Chemical Patents Inc., Houston, TX (US)

(*) Notice: Subject to any disclaimer, the term of this patent is extended or adjusted under 35 U.S.C. 154(b) by 447 days.

(21) Appl. No.: 10/499,794

(22) PCT Filed: Dec. 20, 2002

(86) PCT No.: PCT/US02/40768

§ 371 (c)(1),
(2), (4) Date: Jun. 22, 2004

(87) PCT Pub. No.: WO03/056281

PCT Pub. Date: Jul. 10, 2003

(65) Prior Publication Data

US 2005/0029457 A1 Feb. 10, 2005

Related U.S. Application Data

(60) Provisional application No. 60/346,095, filed on Jan. 1, 2002.

(51) Int. Cl.
*G01N 21/00* (2006.01)
(52) U.S. Cl. .............................................. 250/339.09
(58) Field of Classification Search ............ 250/339.09
See application file for complete search history.

(56) References Cited

U.S. PATENT DOCUMENTS

| 5,528,036 | A | 6/1996 | Achter et al. ............ 250/339.12 |
| 5,977,529 | A * | 11/1999 | Willert-Porada et al. ... 219/698 |
| 6,072,576 | A | 6/2000 | McDonald et al. ......... 256/300 |
| 6,223,133 | B1 | 4/2001 | Brown ........................ 702/85 |
| 6,507,401 | B1 * | 1/2003 | Turner et al. ............... 356/436 |
| 6,512,580 | B1 | 1/2003 | Behringer et al. .......... 356/244 |

FOREIGN PATENT DOCUMENTS

| DE | 10005130 | 8/2001 |
| WO | WO98/29787 | 7/1998 |

* cited by examiner

*Primary Examiner*—David Porta
*Assistant Examiner*—Christine Sung

(57) ABSTRACT

The invention is a method and apparatus for on-line measurement of polymer properties such as moisture content, ethylene content, Epoxidized Soy Bean Oil (ESBO) content, calcium stearate content and ethylidene norbornene (ENB) content.

22 Claims, 1 Drawing Sheet

METHOD AND APPARATUS FOR ON-LINE MEASUREMENT OF POLYMER PROPERTIES

This application is the National Stage of International Application No. PCT/US02/40768, filed Dec. 20, 2002, which claims the benefit of U.S. Provisional Application No. 60/346,095, filed Jan. 1, 2002, the entire disclosure of which is hereby incorporated herein by reference.

FIELD OF THE INVENTION

The invention relates to a method and apparatus for on-line measurement of polymer properties. More particularly, the polymer properties measured include, but are not limited to, moisture content, ethylene content, Epoxidized Soy Bean Oil (ESBO) content, calcium stearate content and ethylidene norbornene (ENB) content.

BACKGROUND

Measurement of polymer moisture content and other polymer properties during the finishing process of polymer production is important to ensure that the product meets particular specifications. The measurement is particularly important for detecting grade switches, wherein production of one polymer having specific properties ends and production of another polymer having different properties begins. It is important to accurately detect the transition from the old grade to the new grade in order to properly label the product and reset the finishing plant controls for the new grade in a timely manner.

One of the previous methods of measuring polymer properties involves taking a sample from the process line and running tests in the laboratory. The major disadvantage of this approach is the long delay between taking the sample and receiving the results of the analysis. This delay can be at least one to two hours. The time delay leads to off-specification product, which, in turn, leads to less profit. The time delay also makes it difficult to optimize control of the process due to the delay in resetting the controls.

Another method of measuring polymer properties is the use of Fourier Transform Near-Infrared spectrometer (FT-NIR) photometers. These devices permit measurement of moisture content while the polymer is on a conveyor line, but they do not allow for the measurement of other polymer properties. Photometer-based technology is also limited by its ability to provide a moisture value that only trends actual moisture variation in the polymer, rather than the highly accurate polymer moisture value resulting from the method of the present invention.

Yet another method of measuring polymer properties is the use of multi-wavelength dispersive-type spectrometers. These devices have been used on conveyor lines in a non-contact configuration, allowing for on-line measurements, but they provide inferior measurement accuracy and calibration stability as compared to the FTNIR spectrometer.

Prior methods of measuring polymer properties have either been inefficient due to time delays or have resulted in measurements that merely trend, rather than accurately measure, the value of the property. A need therefore exists for obtaining stable, accurate, real-time measurements of moisture content and other properties of polymers while the polymer is on the conveyor line.

SUMMARY OF THE INVENTION

One embodiment of the invention relates to a method for measuring a property of a test sample comprising (a) providing a corrected set of measured spectra for a set of calibration samples by (i) obtaining a set of measured spectra for a set of calibration samples, and (ii) performing constrained principal spectral analysis on said calibration samples to provide a corrected set of measured spectra, (b) providing said test sample having an unknown value of said property, (c) applying light to said test sample resulting in reflected light, (d) detecting said reflected light, (e) transmitting said reflected light to a spectrometer, (f) measuring a spectrum for said test sample, (g) performing constrained principal spectral analysis on said test sample spectrum to provide a corrected test sample spectrum, (h) performing locally weighted regression analysis by selecting a subset of said corrected calibration sample spectra and building a regression model based upon said selected subset, and (i) predicting a value for said unknown property of said test sample using said corrected test sample spectrum and said regression model. Properties that can be measured include, but are not limited to moisture content, ethylene content, Epoxidized Soy Bean Oil (ESBO) content, calcium stearate content, and ethylidene norbornene (ENB) content.

In another embodiment, the invention is an apparatus for analyzing at least one property of a sample comprising, (a) a conveying device for conveying the sample along a predetermined path of travel through an inspection zone, (b) a light source associated with the inspection zone for emitting light onto said sample, wherein said light source is not in contact with said sample, (c) light collection optics associated with the inspection zone for detecting light reflected off of the sample, (d) at least one fiber optic cable for transmitting the reflected light from the light collection optics to a spectrometer, (e) a spectrometer located remotely from the conveying device for generating a reflectance spectrum, and (f) a computer adapted to: (i) derive a predictive model relating the reflectance spectrum and the property of said sample, and (ii) predict a value for said property of said sample from said predictive model and said reflectance spectrum.

In yet another embodiment, the invention relates to a method for online control of a process to produce a product with a property P and having a desired value D comprising (a) obtaining a set of measured spectra for a set of calibration samples, (b) performing constrained principal spectral analysis on the set of measured spectra for the set of calibration samples to produce corrected spectra for the set of calibration samples, (c) providing a test sample having an unknown value of said property P, (d) applying light to said test sample resulting in reflected light, (e) detecting said reflected light, (f) transmitting the reflected light to a spectrometer, (g) measuring a spectrum for the test sample, (h) performing constrained principal spectral analysis on the test sample spectrum to produce a corrected test sample spectrum, (i) performing locally weighted regression analysis by selecting a subset of the corrected calibration sample spectra and building a regression model based upon the selected subset, (j) predicting a value for said property P of said test sample using the corrected test sample spectrum and the regression model, (k) adjusting the process parameters based upon the difference in the predicted value of said property P and the desired value D.

In yet another embodiment, the invention is a method for online detection of a change from a first polymer grade to a second polymer grade in a polymer finishing process comprising (a) obtaining a set of measured spectra far a set of calibration samples, (b) performing constrained principal spectral analysis on said set of measured spectra to produce corrected spectra for said set of calibration samples, (c) assigning a grade type to each said corrected spectrum of said set of calibration samples, (d) applying light to a polymer sample in said polymer finishing process resulting in reflected light, (e) detecting said reflected light, (f) transmitting said reflected light to a spectrometer, (g) measuring a spectrum for said polymer sample, (h) performing constrained principal spectral analysis on said polymer sample spectrum to provide a corrected polymer sample spectrum, (i) performing K-nearest neighbor analysis on said corrected polymer sample spectrum comprising selecting a subset of said corrected calibration spectra based upon the similarity of said subset spectra to said corrected polymer sample spectrum, and counting the assigned grade type of each said corrected calibration spectrum in said subset, (j) assigning a grade type to said polymer sample based upon said count, and (k) comparing said assigned grade type to said polymer sample with said first polymer grade.

In yet another embodiment, the invention is a method for online control of a polymer finishing process resulting from a change from a first polymer grade to a second polymer grade comprising (a) obtaining a set of measured spectra for a set of calibration samples, (b) performing constrained principal spectral analysis on said set of measured spectra to produce corrected spectra for said set of calibration samples, (c) assigning a grade type to each said corrected spectrum of said set of calibration samples, (d) providing a test sample having an unknown grade type, (e) applying light to said test sample resulting in reflected light, (f) detecting said reflected light, (g) transmitting said reflected light to a spectrometer, (h) measuring a spectrum for said test sample, (i) performing K-nearest neighbor analysis on said test sample spectrum comprising selecting a subset of corrected calibration spectra from said set of corrected calibration spectra based upon the similarity of said subset spectra to said test sample spectrum, counting the assigned grade type of each said corrected spectrum in said subset, and assigning a grade type to said test sample based upon the comparison to said subset, and (j) if necessary, altering the conditions of said finishing process for said second polymer grade.

DETAILED DESCRIPTION

Figure 1:
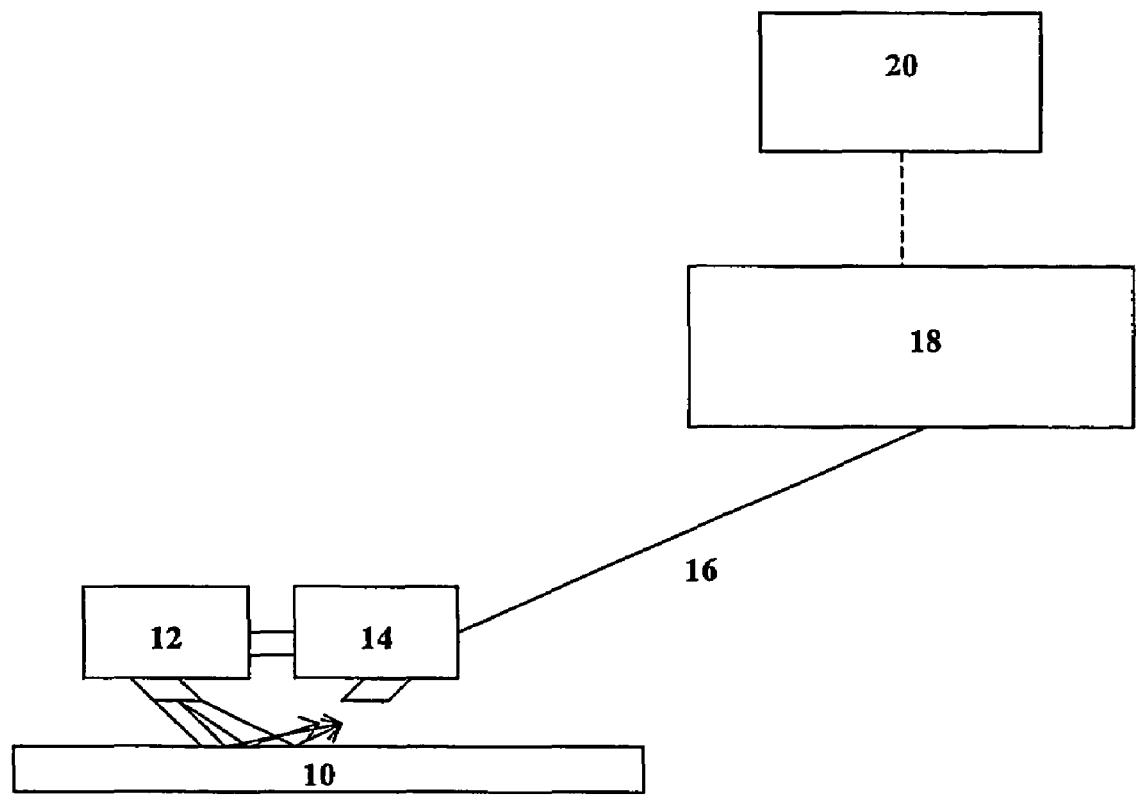
FIG. 1 presents a schematic representation of one embodiment of the invention.

The method and apparatus described herein involve the measurement of polymer properties through spectroscopic analysis. Spectroscopic analysis generally involves the identification of elements and elucidation of atomic and molecular structure by illuminating or irradiating the substance under examination and then measuring the radiant energy absorbed or emitted by the substance. The energy absorbed or emitted may be in any of the wavelengths of the electromagnetic spectrum. By comparing and/or correlating the measured wavelengths absorbed or emitted by the sample with wavelengths absorbed or emitted from known elements or molecules, information about a sample may be determined.

Apparatus

In one embodiment, an apparatus for the on-line analysis of polymers is provided. A particular embodiment includes an apparatus for ascertaining the moisture content, ethylene content, epoxidized soybean oil (ESBO) content, calcium stearate content, and ethylidene norbornene (ENB) content of crumb rubber on a conveyor. Use of the term rubber herein is descriptive of all elastomeric polymers and plastics, and includes ethylene-propylene-diene monomer rubber (EPDM), ethylene propylene rubber (EPR), butyl rubber, halobutyl rubber, styrene-isoprene-styrene (SIS), styrene-butadiene copolymers (SBC), poly-isoprene rubber, poly-isobutylene rubber (PIB), styrene-butadiene-styrene (SBS), styrene-butadiene rubber (SBR), poly-butadiene rubber (BR), blends of said elastomeric polymers as well as blends of these rubbers with thermoplastics.

Referring now to FIG. 1, the apparatus comprises a conveyor 10, a light source 12, light collection optics 14, at least one fiber optic cable 16, a spectrometer 18, and a computer 20. The conveyor 10 includes any device that is suitable for conveying material, particularly solid material, along a predetermined path through an inspection zone. Examples of conveyors include, but are not limited to a conveyor belt, a belt puller, and rollers. In one embodiment, the conveyor is a vibrating conveyor belt suitable for transporting crumb rubber. An example of a suitable vibrating conveyor belt is a type IBHR Fluid Bed conveyor (Isolated Balanced Heavy-duty with Rocker arms and shock absorbers) available from Carrier Vibrating Equipment, Inc. of Louisville, Ky.

The term "inspection zone" generally refers to an area through which a sample passes wherein light is emitted and reflected off of a sample. Associated with the inspection zone is the light source 12 and light collection optics 14, collectively referred to as the "sensor equipment," which are mounted above the conveyor 10 in a position so that they are not in contact with the material on the conveyor 10, and so that light emitted by the light source 12 may be reflected off of the material on the conveyor 10 and detected by the light collection optics 14. Preferably, the distance from the material on the conveyor to the sensor equipment is from about 10 to about 16 inches.

The light source 12 and light collection optics 14 may be contained in a separate housing units or single housing unit. The housing unit may be made of any suitable material, such as metal. An example of a suitable configuration of a light source and light collection optics in a housing unit is the ReflectIR module available from Orbital Sciences of Pomona, Calif.

In one embodiment, the sensor equipment is mounted to an instrument stand-pipe. The mount allows the sensor equipment to be displaced for access to the conveyor, for example for cleaning and plug removal. Suitable mounts include, but are not limited to a u-joint connection and swing arm. The u-joint connection also allows the sensor equipment to be repeatedly returned to its original location if moved.

In an embodiment of the invention, the light source 12 comprises from 1 to 3 infrared-emitting light bulbs. The light source 12 and light collection optics 14 are preferably located in the finishing unit of a rubber processing plant at a point after the crumb exits the extruder and before the crumb enters the bailer.

At least one fiber optic cable 16 is used to connect the light source 12 and light collection optics 14 to a spectrometer 18. The use of at least one fiber optic cable 16 allows the spectrometer 18 to be located in an area that is remote from the light source 12 and light collection optics 14. It is desirable to locate the spectrometer 18 remotely from the light source 12 and light collection optics 14 because the spectrometer contains an internal laser that is susceptible to vibration, which may be present on the production floor where the light source 12 and light collection optics 14 are located.

In one embodiment, the spectrometer 18 is a Fourier Transform Infrared (FTNIR) spectrometer. In another embodiment, the spectrometer 18 is a PCM1000 FTNIR Analyzer available from Orbital Sciences of Pomona, Calif.

In another embodiment, the apparatus comprises multiple conveyors, each conveyor having a light source and light collection optics in a location as described above for a single conveyor. At least one fiber optic cable is used to connect the light source and light collection optics of the multiple conveyors to a single spectrometer.

The spectrum generated by the spectrometer 18 is processed by a computer 20, which is discussed further below. One of ordinary skill in the art would understand the light source 12, light collection optics 14, fiber optic cable 16, and spectrometer 18, as they are commonly known in the market.

Data Analysis

The method and apparatus described in this specification involve an analytical measurement technique based on near-infrared (NIR) spectroscopy, which uses electromagnetic radiation in the near-infrared region. NIR refers to wavelengths in the region of from approximately 500 to 2500 nm.

In the NIR spectroscopy discussed herein, the radiation from a light source is directed at a sample on a conveying means. Because the samples described herein are opaque, the light is reflected off of rather than absorbed by the sample. Next, the reflected light is detected by the light collection optics and transmitted through at least one fiber optic cable to a spectrometer. The spectrometer converts the reflected light into a reflectance spectrum in which the amount of radiation reflected is plotted as a function of wavelength. The reflectance spectrum is then transmitted to a data analysis device, for example a computer, for further processing, as discussed below. The method of transmitting the spectra to the data analysis device is not crucial to the invention. For example, data can be transferred by cable, by diskette or any other appropriate means.

It is well recognized that chemical and physical information of samples can be obtained through spectral reflectance data. Because each composition in the sample will have a characteristic reflectance spectrum, the NIR spectra reflect the chemical composition of the compound(s) measured.

The NIR reflectance spectrum of a typical elastomer contains extensively overlapping bands, which represent the reflectance features that are associated with each of the components of interest. The overlapping bands preclude the use of simple univariate calibration methods for quantitation of the sample components. This problem is overcome by applying multivariate mathematical calibration techniques to the analysis of the spectral data. These well-known multivariate mathematical techniques use complex mathematics such as matrix vector algebra and statistics to extract quantitative information, for example concentrations, from highly convoluted or statistically confounded data. Non-limiting examples of multivariate mathematical techniques are partial least squares (PLS), locally weighted regression (LWR), and combinations thereof.

Multivariate mathematical techniques are typically performed in general purpose computers suitable for running commercially available software programs. Numerous software packages are currently available. Examples of the available software packages include, but are not limited to "AnaGrams," available from Orbital Sciences of Pomona, Calif.; MATLAB™, available from The Math Works, Inc., of Natick, Mass.; Pirouette™, available from Infometrix, Inc., of Woodinville, Wash.; and Spectral ID™, available from Thermo Galactic, of Salem, N.H. Preferably, the computer 20 is configured with a processor having capabilities that are at least commensurate with that of the 100 MHz Intel Pentium processor, and having at least 8 Megabytes of memory. In general, more rather than less memory is preferred, and higher rather than lower speed processors are preferred to enable analysis of large amounts of wavelength data in real time during a process being monitored.

In practice, quantitative NIR analysis using these mathematical techniques requires fairly extensive calibration. This calibration is achieved by analyzing a set of calibration samples with known values for all of the properties to be measured by NIR. The results for the calibration sample set are used to build a calibration model using the multivariate calibration procedure. Once a suitable model is built, it is used to calculate the property or properties of interest from the NIR reflectance spectra of samples with unknown properties.

In one embodiment, the data analysis further includes using the apparatus of the current invention to correct spectral data for errors that result from the spectral measurement process itself. U.S. Pat. No. 5,121,337, hereby incorporated by reference, discloses a process, hereinafter referred to as Constrained Principal Spectral Analysis or "CPSA," for correcting spectral data for data due to the spectral measurement process and estimating unknown property and/or composition data of a sample using such method.

In a particular embodiment, the invention involves measurement of a single property in the presence of a wide variation of unmeasured properties. In this embodiment, the CPSA correction is performed followed by the LWR multivariate mathematical technique. As is known to those of ordinary skill in the art, LWR is a variant of the least squares regression method. However, unlike linear regression methods which develop regression coefficients from the entire calibration sample set, the LWR technique follows preset rules to select a subset of samples (from the calibration set) that are similar to the unknown sample in order to produce a local (subset) regression just for the unknown property. Typical selection rules for the subset is by classification or cluster analysis, which is commonly practiced in statistical data analysis, for example Principal Components Analysis. The sample selection and regression calculation are repeated for every unknown sample to generate a set of regression coefficients specific for every new unknown. Accordingly, the combination of performing CPSA followed by LWR builds models "on the fly," that is, by providing a different and constantly changing set of calibration samples for each prediction of an unknown spectra, as opposed to those regression models using a static calibration set with fixed regression coefficients for the unknown predictions. This LWR technique is especially useful for the measurement of a property such as moisture, ethylene, ENB, ESBO, and calcium stearate content in an elastomeric or other polymer that has a widely varying underlying chemical composition or structure that is not directly associated with the measured property.

The initial model can be further improved with off-line spectral data for various elastomer grades, or can be upgraded after actual use with data generated on different elastomer grades on the conveyor. As more on-line data becomes available, the on-line data can be used to replace the original off-line data in the mathematical model. Eventual replacement of the off-line data with on-line data, including data on various elastomer grades, results in a highly accurate property analysis. In one embodiment, the measurements resulting from the process of the present invention are used to detect grade switches of polymer and reset the finishing process controls for the new grade. In another embodiment, the measurements are used to determine whether the product is off-specification. In a preferred embodiment, product grade change and/or the presence of off-specification product is determined by performing CPSA analysis followed by K-nearest neighbor (KNN) analysis. As is known to those of ordinary skill in the art, KNN is a similarity-based classification method that categorizes groups of samples according to their similarity in the measurement space. After the CPSA is performed, the unknown sample is classified, or grade-predicted, by comparing the sample to a number of similar training samples having a predetermined classification or grade type based on distance (or similarity) of the unknown to the calibration set. The use of the CPSA technique as a pre-processing step prior to the KNN analysis provides for much improved classification analysis due to the removal of unwanted instrumental and spectral variation not associated with the class of the polymer. This method allows for a more robust automated detection of grade change, which allows for precise and timely resetting of finishing unit equipment for the new grade of polymer.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

What is claimed is:

1. A method for measuring a property of a test sample comprising:
    a) obtaining a set of measured spectra for a set of calibration samples, and performing constrained principal spectral analysis on said calibration samples to provide a corrected set of measured spectra,
    b) providing said test sample having an unknown value of said property,
    c) applying light to said test sample resulting in reflected light,
    d) detecting said reflected light,
    e) transmitting said reflected light to a spectrometer,
    f) measuring a spectrum for said test sample,
    g) performing constrained principal spectral analysis on said test sample spectrum to provide a corrected test sample spectrum,
    h) performing locally weighted regression analysis by selecting a subset of said corrected calibration sample spectra and building a regression model based upon said selected subset, and
    i) predicting a value for said unknown property of said test sample using said corrected test sample spectrum and said regression model.

2. The method of claim 1, wherein said property is selected from the group consisting of moisture content, ethylene content, Epoxidized Soy Bean Oil (ESBO) content, calcium stearate content, and ethylidene norbornene (ENB) content.

3. The method of claim 1, wherein said test sample comprises a polymer.

4. The method of claim 1, wherein said test sample comprises a rubber.

5. The method of claim 1, wherein said measured spectra for said set of calibration samples comprise reflectance spectra in the near infrared region.

6. The method of claim 1, wherein said test sample spectrum comprises reflectance spectra in the near infrared region.

7. The method of claim 5 or 6, wherein said measurement of near infrared spectra is made by a Fourier Transform Near Infrared (FTNIR) spectrometer.

8. The method of claim 1, wherein said measurement of said spectrum for said test sample is performed at least once every minute.

9. A method for online control of a process to produce a product with a property P and having a desired value D, said method comprising:
    a) obtaining a set of measured spectra for a set of calibration samples,
    b) performing constrained principal spectral analysis on said set of measured spectra for said set of calibration samples to produce corrected spectra for said set of calibration samples,
    c) providing a test sample having an unknown value of said property P,
    d) applying light to said test sample resulting in reflected light,
    e) detecting said reflected light,
    f) transmitting said reflected light to a spectrometer,
    g) measuring a spectrum for said test sample,
    h) performing constrained principal spectral analysis on said test sample spectrum to produce a corrected test sample spectrum,
    i) performing locally weighted regression analysis by selecting a subset of said corrected calibration sample spectra and building a regression model based upon said selected subset,
    j) predicting a value for said property P of said test sample using said corrected test sample spectrum and said regression model,
    k) adjusting the process parameters based upon the difference in the predicted value of said property P and desired value D.

10. The method of claim 9, wherein said subset is selected based upon at least one of classification analysis and cluster analysis.

11. The method of claim 9, wherein said property is selected from moisture content, ethylene content, Epoxidized Soy Bean Oil (ESBO) content, calcium stearate content, and ethylidene norbornene (ENB) content.

12. The method of claim 9, wherein said test sample is a polymer.

13. The method of claim 9, wherein said test sample comprises a rubber.

14. The method of claim 9, wherein said measured spectra for said set of calibration samples comprise reflectance spectra in the near infrared region.

15. The method of claim 9, wherein said test sample spectrum comprises reflectance spectra in the near infrared region.

16. The method of claim 9, wherein said measurement of near infrared spectra is made by a Fourier Transform Near Infrared (FTNIR) spectrometer.

17. The method of claim 9, wherein said measurement of said spectrum for said test sample is performed at least once every minute.

18. A method for online detection of a change from a first polymer grade to a second polymer grade in a polymer finishing process comprising:

a) obtaining a set of measured spectra for a set of calibration samples,
b) performing constrained principal spectral analysis on said set of measured spectra to produce corrected spectra for said set of calibration samples,
c) assigning a grade type to each said corrected spectrum of said set of calibration samples,
d) applying light to a polymer sample in said polymer finishing process resulting in reflected light,
e) detecting said reflected light,
f) transmitting said reflected light to a spectrometer,
g) measuring a spectrum for said polymer sample,
h) performing constrained principal spectral analysis on said polymer sample spectrum to provide a corrected polymer sample spectrum,
i) performing K-nearest neighbor analysis on said corrected polymer sample spectrum comprising selecting a subset of said corrected calibration spectra based upon the similarity of said corrected subset spectra to said corrected polymer sample spectrum, and counting the assigned grade type of each said corrected calibration spectrum in said subset,
j) assigning a grade type to said polymer sample based upon said count, and
k) comparing said assigned grade type to said polymer sample with said first polymer grade.

19. The method of claim 18, wherein said measurement of near infrared spectra is made by a Fourier Transform Near Infrared (FTNIR) spectrometer.

20. A method for online control of a polymer finishing process resulting from a change from a first polymer grade to a second polymer grade comprising:

a) obtaining a set of measured spectra for a set of calibration samples,
b) performing constrained principal spectral analysis on said set of measured spectra to produce corrected spectra for said set of calibration samples,
c) assigning a grade type to each said corrected spectrum of said set of calibration samples,
d) providing a test sample having an unknown grade type,
e) applying light to said test sample resulting in reflected light,
f) detecting said reflected light,
g) transmitting said reflected light to a spectrometer,
h) measuring a spectrum for said test sample,
i) performing K-nearest neighbor analysis on said test sample spectrum comprising selecting a subset of corrected calibration spectra from said set of corrected calibration spectra based upon the similarity of said subset spectra to said test sample spectrum, counting the assigned grade type of each said corrected spectrum in said subset, and
j) assigning a grade type to said test sample based upon the comparison to said subset.

21. The method of claim 20, wherein said measurement of near infrared spectra is made by a Fourier Transform Near Infrared (FTNIR) spectrometer.

22. The method of claim 20, further comprising:

k) altering the conditions of said finishing process for said second polymer grade.

* * * * *